(12) United States Patent
Bojan et al.

(10) Patent No.: US 8,567,235 B2
(45) Date of Patent: Oct. 29, 2013

(54) TUBE MEASUREMENT TECHNIQUE USING LINEAR ACTUATOR AND PRESSURE SENSOR

(75) Inventors: Peter M. Bojan, Grayslake, IL (US); Zhengyan Wang, Antioch, IL (US); Surya Rai, Lake Bluff, IL (US); Paul Olczak, Evanston, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 573 days.

(21) Appl. No.: 12/826,192

(22) Filed: Jun. 29, 2010

(65) Prior Publication Data

US 2011/0319823 A1    Dec. 29, 2011

(51) Int. Cl.
*G01M 3/02* (2006.01)
(52) U.S. Cl.
USPC ............................................................ 73/37
(58) Field of Classification Search
USPC ............................................................ 73/37
See application file for complete search history.

(56) References Cited

U.S. PATENT DOCUMENTS

| | | |
|---|---|---|
| 3,606,596 A | 9/1971 | Edwards |
| 3,756,752 A | 9/1973 | Stenner |
| 3,771,694 A | 11/1973 | Kaminski |
| 3,809,871 A | 5/1974 | Howard et al. |
| 3,998,103 A | 12/1976 | Bjorklund et al. |
| 4,038,983 A | 8/1977 | Mittleman et al. |
| D246,258 S | 11/1977 | Ekert |
| 4,065,230 A | 12/1977 | Gezari |
| 4,078,562 A | 3/1978 | Friedman |
| 4,151,407 A | 4/1979 | McBride et al. |
| 4,187,057 A | 2/1980 | Xanthopoulos |
| 4,199,307 A | 4/1980 | Jassawalla |
| 4,237,409 A | 12/1980 | Sugalski |
| 4,256,437 A | 3/1981 | Brown |
| 4,273,121 A | 6/1981 | Jassawalla |
| 4,276,004 A | 6/1981 | Hahn |
| 4,277,226 A | 7/1981 | Archibald |
| 4,308,866 A | 1/1982 | Jelliffe et al. |

(Continued)

FOREIGN PATENT DOCUMENTS

| | | |
|---|---|---|
| EP | 0044823 | 1/1982 |
| EP | 0215249 | 3/1987 |

(Continued)

OTHER PUBLICATIONS

International Search Report for International Application No. PCT/US 02/36963 of Applicant Baxter International Inc.

(Continued)

*Primary Examiner* — Hezron E Williams
*Assistant Examiner* — Rodney T Frank
(74) *Attorney, Agent, or Firm* — K&L Gates LLP

(57) ABSTRACT

An infusion pump uses sensors, movable members and a control unit to determine tubing thickness in a tube-loading section of the pump. The infusion pump utilizes sensors, such as a pressure sensor, to record forces imparted by a tube undergoing no pressure, a single pressure, or a pressure sweep, to determine thickness. Using these values, the tubing wall thickness can be determined. The infusion pump can also compress a tube using a movable member of the pump and records the distance traveled by the movable member to compress fully the tube. Using this distance, the tubing wall thickness can be determined.

21 Claims, 4 Drawing Sheets

(56) References Cited

U.S. PATENT DOCUMENTS

| | | |
|---|---|---|
| 4,320,757 A | 3/1982 | Whitney et al. |
| D263,997 S | 4/1982 | Preussner |
| 4,332,246 A | 6/1982 | Thomson |
| 4,369,780 A | 1/1983 | Sakai |
| 4,373,525 A | 2/1983 | Kobayashi |
| D268,206 S | 3/1983 | Kosako |
| 4,392,849 A | 7/1983 | Petre et al. |
| 4,398,908 A | 8/1983 | Siposs |
| 4,416,595 A | 11/1983 | Cromie |
| 4,428,381 A | 1/1984 | Hepp |
| 4,430,078 A | 2/1984 | Sprague |
| 4,443,216 A | 4/1984 | Chappell |
| 4,445,535 A | 5/1984 | Mayfield |
| 4,447,233 A | 5/1984 | Mayfield |
| 4,447,234 A | 5/1984 | Mayfield |
| 4,451,255 A | 5/1984 | Bujan et al. |
| 4,457,751 A | 7/1984 | Rodler |
| 4,460,358 A | 7/1984 | Somerville et al. |
| 4,468,221 A | 8/1984 | Mayfield |
| 4,472,116 A | 9/1984 | Wenstrup |
| 4,487,604 A | 12/1984 | Iwatschenko et al. |
| 4,493,710 A | 1/1985 | King et al. |
| 4,496,351 A | 1/1985 | Hillell et al. |
| 4,498,843 A | 2/1985 | Schneider et al. |
| D278,181 S | 3/1985 | Archibald et al. |
| 4,504,200 A | 3/1985 | Olson |
| 4,511,352 A | 4/1985 | Theeuwes et al. |
| D278,743 S | 5/1985 | Manno et al. |
| 4,519,792 A | 5/1985 | Dawe |
| 4,529,401 A | 7/1985 | Leslie et al. |
| 4,537,561 A | 8/1985 | Xanthopoulos |
| 4,544,369 A | 10/1985 | Skakoon et al. |
| 4,551,133 A | 11/1985 | Zegers de Beyl et al. |
| 4,559,038 A | 12/1985 | Berg et al. |
| 4,561,830 A | 12/1985 | Bradley |
| 4,561,856 A | 12/1985 | Cochran |
| 4,562,751 A | 1/1986 | Nason et al. |
| 4,565,542 A | 1/1986 | Berg |
| 4,578,868 A | 4/1986 | Sasaki et al. |
| 4,585,009 A | 4/1986 | Barker et al. |
| 4,585,941 A | 4/1986 | Bergner |
| 4,596,550 A | 6/1986 | Troutner |
| 4,601,702 A | 7/1986 | Hudson |
| 4,602,249 A | 7/1986 | Abbott |
| 4,624,661 A | 11/1986 | Arimond |
| D287,053 S | 12/1986 | Bucchianeri et al. |
| D287,277 S | 12/1986 | Kosako et al. |
| 4,637,817 A | 1/1987 | Archibald et al. |
| 4,639,245 A | 1/1987 | Pastrone et al. |
| 4,646,781 A | 3/1987 | McIntyre et al. |
| 4,648,812 A | 3/1987 | Kobayashi et al. |
| 4,650,469 A | 3/1987 | Berg et al. |
| 4,652,262 A | 3/1987 | Veracchi |
| 4,653,987 A | 3/1987 | Tsuji et al. |
| 4,657,490 A | 4/1987 | Abbott |
| 4,666,430 A | 5/1987 | Brown et al. |
| 4,668,220 A | 5/1987 | Hawrylenko |
| 4,676,776 A | 6/1987 | Howson |
| 4,678,408 A | 7/1987 | Nason et al. |
| 4,681,563 A | 7/1987 | Deckert et al. |
| 4,685,903 A | 8/1987 | Cable et al. |
| 4,690,673 A | 9/1987 | Bloomquist |
| 4,696,671 A | 9/1987 | Epstein et al. |
| D293,468 S | 12/1987 | Hill et al. |
| 4,714,462 A | 12/1987 | DiDomenico |
| 4,718,576 A | 1/1988 | Tamura et al. |
| 4,718,893 A | 1/1988 | Dorman et al. |
| 4,722,149 A | 2/1988 | Weaver et al. |
| 4,722,224 A | 2/1988 | Scheller et al. |
| 4,722,734 A | 2/1988 | Kolln |
| 4,725,205 A | 2/1988 | Cannon et al. |
| 4,731,058 A | 3/1988 | Doan |
| D295,320 S | 4/1988 | Vaughan |
| 4,741,732 A | 5/1988 | Crankshaw et al. |
| 4,741,736 A | 5/1988 | Brown |
| 4,744,786 A | 5/1988 | Hooven |
| 4,754,401 A | 6/1988 | Kaczynski et al. |
| 4,756,706 A | 7/1988 | Kerns et al. |
| 4,758,228 A | 7/1988 | Williams |
| 4,759,527 A | 7/1988 | Brown |
| 4,772,263 A | 9/1988 | Dorman et al. |
| 4,781,548 A | 11/1988 | Alderson et al. |
| 4,804,368 A | 2/1989 | Skakoon et al. |
| 4,810,243 A | 3/1989 | Howson |
| 4,834,704 A | 5/1989 | Reinicke |
| 4,836,752 A | 6/1989 | Burkett |
| 4,838,857 A | 6/1989 | Strowe et al. |
| 4,838,860 A | 6/1989 | Groshong et al. |
| 4,840,542 A | 6/1989 | Abbott |
| 4,845,646 A | 7/1989 | Marquis et al. |
| 4,846,637 A | 7/1989 | Alderson et al. |
| 4,854,324 A | 8/1989 | Hirschman et al. |
| 4,856,339 A | 8/1989 | Williams |
| 4,882,575 A | 11/1989 | Kawahara |
| D305,060 S | 12/1989 | Bisha' et al. |
| 4,886,431 A | 12/1989 | Soderquist et al. |
| 4,890,984 A | 1/1990 | Alderson et al. |
| 4,898,579 A | 2/1990 | Groshong et al. |
| 4,900,305 A | 2/1990 | Smith et al. |
| 4,908,017 A | 3/1990 | Howson et al. |
| 4,911,168 A | 3/1990 | Davis |
| 4,919,650 A | 4/1990 | Feingold et al. |
| 4,923,375 A | 5/1990 | Ejlersen |
| 4,931,041 A | 6/1990 | Faeser |
| 4,936,760 A | 6/1990 | Williams |
| D309,662 S | 7/1990 | Gorton |
| 4,941,808 A | 7/1990 | Qureshi et al. |
| 4,943,279 A | 7/1990 | Samiotes et al. |
| 4,954,046 A | 9/1990 | Irvin et al. |
| 4,960,230 A | 10/1990 | Marelli |
| 4,976,151 A | 12/1990 | Morishita |
| 4,978,335 A | 12/1990 | Arthur, III |
| 5,000,739 A | 3/1991 | Kulisz et al. |
| 5,006,050 A | 4/1991 | Cooke et al. |
| 5,011,378 A | 4/1991 | Brown et al. |
| 5,017,192 A | 5/1991 | Dodge et al. |
| 5,034,004 A | 7/1991 | Crankshaw |
| 5,041,086 A | 8/1991 | Koenig et al. |
| 5,044,900 A | 9/1991 | Cavallaro |
| 5,049,047 A * | 9/1991 | Polaschegg et al. .......... 417/474 |
| 5,053,031 A | 10/1991 | Borsanyi |
| 5,055,001 A | 10/1991 | Natwick et al. |
| 5,057,081 A | 10/1991 | Sunderland et al. |
| 5,061,243 A | 10/1991 | Winchell et al. |
| D321,559 S | 11/1991 | Kienholz |
| 5,078,362 A | 1/1992 | Lawless et al. |
| 5,078,683 A | 1/1992 | Sancoff et al. |
| 5,080,653 A | 1/1992 | Voss et al. |
| 5,088,904 A | 2/1992 | Okada |
| 5,098,256 A | 3/1992 | Smith |
| 5,098,377 A | 3/1992 | Borsanyi et al. |
| 5,100,380 A | 3/1992 | Epstein et al. |
| 5,100,389 A | 3/1992 | Vaillancourt |
| 5,102,392 A | 4/1992 | Sakai et al. |
| 5,104,374 A | 4/1992 | Bishko et al. |
| D326,153 S | 5/1992 | Eastman et al. |
| 5,116,203 A | 5/1992 | Natwick et al. |
| 5,120,096 A | 6/1992 | D'Silva |
| 5,123,275 A | 6/1992 | Daoud et al. |
| 5,131,816 A | 7/1992 | Brown et al. |
| D328,952 S | 8/1992 | Arioka |
| 5,135,500 A | 8/1992 | Zdeb |
| 5,153,827 A | 10/1992 | Coutre et al. |
| 5,160,320 A | 11/1992 | Yum et al. |
| 5,165,874 A | 11/1992 | Sancoff et al. |
| 5,167,633 A | 12/1992 | Mann et al. |
| 5,176,004 A | 1/1993 | Gaudet |
| 5,176,644 A | 1/1993 | Srisathapat et al. |
| 5,181,842 A | 1/1993 | Sunderland et al. |
| 5,181,910 A | 1/1993 | Scanlon |
| 5,197,322 A | 3/1993 | Indravudh |
| 5,207,645 A | 5/1993 | Ross et al. |
| 5,213,483 A | 5/1993 | Flaherty et al. |
| 5,215,450 A * | 6/1993 | Tamari .......... 417/474 |

(56) References Cited

U.S. PATENT DOCUMENTS

| | | |
|---|---|---|
| 5,217,442 A | 6/1993 | Davis |
| 5,219,327 A | 6/1993 | Okada |
| 5,219,330 A | 6/1993 | Bollish et al. |
| 5,219,331 A | 6/1993 | Vanderveen |
| 5,219,428 A | 6/1993 | Stern |
| 5,232,449 A | 8/1993 | Stern et al. |
| 5,236,416 A | 8/1993 | McDaniel et al. |
| 5,238,001 A | 8/1993 | Gallant et al. |
| D339,193 S | 9/1993 | Thompson et al. |
| 5,242,407 A | 9/1993 | Struble et al. |
| 5,242,408 A | 9/1993 | Jhuboo et al. |
| 5,244,461 A | 9/1993 | Derlien |
| 5,244,463 A | 9/1993 | Cordner, Jr. et al. |
| 5,254,096 A | 10/1993 | Rondelet et al. |
| 5,256,157 A | 10/1993 | Samiotes et al. |
| 5,257,971 A | 11/1993 | Lord et al. |
| 5,261,884 A | 11/1993 | Stern et al. |
| 5,265,431 A | 11/1993 | Gaudet et al. |
| D342,231 S | 12/1993 | Walker et al. |
| 5,276,610 A | 1/1994 | Maeda et al. |
| 5,279,556 A | 1/1994 | Goi et al. |
| 5,281,111 A | 1/1994 | Plambeck et al. |
| 5,290,239 A | 3/1994 | Classey et al. |
| 5,295,966 A | 3/1994 | Stern et al. |
| 5,295,967 A | 3/1994 | Rondelet et al. |
| 5,298,021 A | 3/1994 | Sherer |
| D347,472 S | 5/1994 | Sunderland et al. |
| 5,308,333 A | 5/1994 | Skakoon |
| 5,308,335 A | 5/1994 | Ross et al. |
| 5,317,506 A | 5/1994 | Coutre et al. |
| D348,101 S | 6/1994 | Poli et al. |
| 5,321,392 A | 6/1994 | Skakoon et al. |
| D348,730 S | 7/1994 | Walker et al. |
| 5,326,236 A | 7/1994 | Kramer et al. |
| 5,328,460 A | 7/1994 | Lord et al. |
| 5,330,431 A | 7/1994 | Herskowitz |
| 5,336,245 A | 8/1994 | Adams et al. |
| 5,338,157 A | 8/1994 | Blomquist |
| 5,341,291 A | 8/1994 | Roizen et al. |
| 5,343,734 A | 9/1994 | Maeda et al. |
| 5,348,539 A | 9/1994 | Herskowitz |
| 5,356,379 A | 10/1994 | Vaillancourt |
| D352,778 S | 11/1994 | Irvin et al. |
| 5,366,904 A | 11/1994 | Qureshi et al. |
| D353,667 S | 12/1994 | Tsubota et al. |
| 5,370,612 A | 12/1994 | Maeda et al. |
| 5,370,622 A | 12/1994 | Livingston et al. |
| 5,374,251 A | 12/1994 | Smith |
| 5,374,965 A | 12/1994 | Kanno |
| 5,376,070 A | 12/1994 | Purvis et al. |
| 5,378,231 A | 1/1995 | Johnson et al. |
| 5,382,236 A | 1/1995 | Otto et al. |
| D355,716 S | 2/1995 | Nash et al. |
| 5,387,088 A | 2/1995 | Knapp et al. |
| 5,389,078 A | 2/1995 | Zalesky et al. |
| 5,395,320 A | 3/1995 | Padda et al. |
| 5,395,324 A | 3/1995 | Hinrichs et al. |
| 5,395,340 A | 3/1995 | Lee |
| 5,397,222 A | 3/1995 | Moss et al. |
| 5,411,482 A | 5/1995 | Campbell |
| 5,415,532 A | 5/1995 | Loughnane et al. |
| 5,419,684 A | 5/1995 | Struble et al. |
| 5,423,746 A | 6/1995 | Burkett et al. |
| 5,423,759 A | 6/1995 | Campbell |
| 5,429,602 A | 7/1995 | Hauser |
| 5,431,627 A | 7/1995 | Pastrone et al. |
| 5,433,704 A | 7/1995 | Ross et al. |
| 5,433,710 A | 7/1995 | VanAntwerp et al. |
| D361,379 S | 8/1995 | Sancoff et al. |
| D361,617 S | 8/1995 | Sancoff et al. |
| 5,437,635 A | 8/1995 | Fields et al. |
| 5,437,642 A | 8/1995 | Thill et al. |
| 5,458,469 A | 10/1995 | Hauser |
| 5,458,578 A | 10/1995 | Sebesta et al. |
| 5,462,051 A | 10/1995 | Oka et al. |
| 5,462,525 A | 10/1995 | Srisathapat et al. |
| 5,466,218 A | 11/1995 | Srisathapat et al. |
| 5,472,317 A | 12/1995 | Field et al. |
| 5,472,420 A | 12/1995 | Campbell |
| 5,478,211 A | 12/1995 | Dominiak et al. |
| 5,482,446 A | 1/1996 | Williamson et al. |
| 5,485,408 A | 1/1996 | Blomquist |
| D367,527 S | 2/1996 | Marston et al. |
| D367,528 S | 2/1996 | Marston et al. |
| 5,489,265 A | 2/1996 | Montalvo et al. |
| 5,501,665 A | 3/1996 | Jhuboo et al. |
| 5,503,538 A | 4/1996 | Wiernicki et al. |
| 5,505,709 A | 4/1996 | Funderburk et al. |
| 5,507,412 A | 4/1996 | Ebert et al. |
| 5,511,951 A | 4/1996 | O'Leary |
| 5,513,957 A | 5/1996 | O'Leary |
| 5,514,103 A | 5/1996 | Srisathapat et al. |
| 5,520,638 A | 5/1996 | O'Quinn et al. |
| D371,194 S | 6/1996 | Marston et al. |
| 5,522,798 A | 6/1996 | Johnson et al. |
| 5,522,799 A | 6/1996 | Furukawa |
| 5,527,307 A | 6/1996 | Srisathapat et al. |
| 5,529,214 A | 6/1996 | Lasonde et al. |
| 5,531,680 A | 7/1996 | Dumas et al. |
| 5,531,697 A | 7/1996 | Olsen et al. |
| 5,533,981 A | 7/1996 | Mandro et al. |
| 5,545,140 A | 8/1996 | Conero et al. |
| 5,547,470 A | 8/1996 | Johnson et al. |
| 5,549,460 A | 8/1996 | O'Leary |
| 5,551,850 A | 9/1996 | Williamson et al. |
| 5,554,115 A | 9/1996 | Thomas et al. |
| 5,554,123 A | 9/1996 | Herskowitz |
| 5,562,621 A | 10/1996 | Claude et al. |
| 5,569,186 A | 10/1996 | Lord et al. |
| 5,573,502 A | 11/1996 | LeCocq et al. |
| 5,573,506 A | 11/1996 | Vasko |
| 5,578,077 A | 11/1996 | Kassatly |
| D376,848 S | 12/1996 | Zelig et al. |
| 5,584,811 A | 12/1996 | Ross et al. |
| 5,586,629 A | 12/1996 | Shoberg et al. |
| 5,588,815 A | 12/1996 | Zaleski, II |
| 5,601,420 A | 2/1997 | Warner et al. |
| 5,609,575 A | 3/1997 | Larson et al. |
| 5,620,312 A | 4/1997 | Hyman et al. |
| RE35,501 E | 5/1997 | Ross et al. |
| 5,628,619 A | 5/1997 | Wilson |
| 5,630,710 A | 5/1997 | Tune et al. |
| D380,260 S | 6/1997 | Hyman |
| 5,637,093 A | 6/1997 | Hyman et al. |
| 5,637,095 A | 6/1997 | Nason et al. |
| 5,643,212 A | 7/1997 | Coutre et al. |
| 5,647,853 A | 7/1997 | Feldmann et al. |
| 5,647,854 A | 7/1997 | Olsen et al. |
| 5,665,070 A | 9/1997 | McPhee |
| 5,669,877 A | 9/1997 | Blomquist |
| 5,673,588 A | 10/1997 | Raymond |
| 5,681,284 A | 10/1997 | Herskowitz |
| 5,681,285 A | 10/1997 | Ford et al. |
| 5,683,367 A | 11/1997 | Jordan et al. |
| 5,685,844 A | 11/1997 | Marttila |
| 5,695,464 A | 12/1997 | Viallet |
| 5,695,473 A | 12/1997 | Olsen |
| D390,654 S | 2/1998 | Alsberg et al. |
| 5,713,856 A | 2/1998 | Eggers et al. |
| 5,722,957 A | 3/1998 | Steinbach |
| 5,743,878 A | 4/1998 | Ross et al. |
| 5,745,378 A | 4/1998 | Barker et al. |
| 5,752,976 A | 5/1998 | Duffin et al. |
| 5,764,034 A | 6/1998 | Bowman et al. |
| 5,766,155 A | 6/1998 | Hyman et al. |
| 5,769,823 A | 6/1998 | Otto |
| 5,776,345 A | 7/1998 | Truitt et al. |
| 5,782,805 A | 7/1998 | Meinzer et al. |
| 5,785,681 A | 7/1998 | Indravudh |
| D397,432 S | 8/1998 | Rake et al. |
| 5,788,669 A | 8/1998 | Peterson |
| 5,791,880 A | 8/1998 | Wilson |
| 5,795,327 A | 8/1998 | Wilson et al. |
| 5,807,322 A * | 9/1998 | Lindsey et al. .................. 604/65 |

(56) References Cited

U.S. PATENT DOCUMENTS

| | | |
|---|---|---|
| 5,807,336 A | 9/1998 | Russo et al. |
| 5,813,972 A | 9/1998 | Nazarian et al. |
| 5,814,015 A | 9/1998 | Gargano et al. |
| 5,814,019 A | 9/1998 | Steinbach et al. |
| 5,836,915 A | 11/1998 | Steinbach et al. |
| 5,840,058 A | 11/1998 | Ammann et al. |
| 5,842,841 A | 12/1998 | Danby et al. |
| D404,813 S | 1/1999 | Hauser |
| 5,868,710 A | 2/1999 | Battiato et al. |
| 5,871,465 A | 2/1999 | Vasko |
| 5,885,245 A | 3/1999 | Lynch et al. |
| D408,911 S | 4/1999 | Moubayed et al. |
| 5,894,273 A | 4/1999 | Meador et al. |
| 5,895,371 A | 4/1999 | Levitas et al. |
| 5,897,530 A | 4/1999 | Jackson |
| 5,904,668 A | 5/1999 | Hyman et al. |
| 5,908,414 A | 6/1999 | Otto et al. |
| 5,935,099 A | 8/1999 | Peterson et al. |
| 5,935,106 A | 8/1999 | Olsen |
| 5,943,633 A | 8/1999 | Wilson et al. |
| 5,951,510 A | 9/1999 | Barak |
| 5,954,696 A | 9/1999 | Ryan |
| 5,954,697 A | 9/1999 | Srisathapat et al. |
| 5,957,890 A | 9/1999 | Mann et al. |
| 5,988,983 A | 11/1999 | Furusawa |
| 5,993,420 A | 11/1999 | Hyman et al. |
| 6,004,020 A | 12/1999 | Bartur |
| 6,013,057 A | 1/2000 | Danby et al. |
| D420,737 S | 2/2000 | Kivlehan |
| 6,024,539 A | 2/2000 | Blomquist |
| 6,078,273 A | 6/2000 | Hutchins et al. |
| 6,083,201 A | 7/2000 | Skinkle |
| D430,288 S | 8/2000 | Mason et al. |
| D430,289 S | 8/2000 | Mason et al. |
| 6,095,757 A | 8/2000 | Frezza |
| 6,106,498 A | 8/2000 | Friedli et al. |
| 6,110,152 A | 8/2000 | Kovelman |
| 6,123,524 A | 9/2000 | Danby et al. |
| 6,129,517 A | 10/2000 | Danby et al. |
| 6,135,949 A | 10/2000 | Russo et al. |
| 6,139,748 A | 10/2000 | Ericson et al. |
| D434,142 S | 11/2000 | Cheney, II et al. |
| 6,145,695 A | 11/2000 | Garrigues |
| 6,173,198 B1 | 1/2001 | Schulze et al. |
| 6,195,887 B1 | 3/2001 | Danby et al. |
| 6,203,528 B1 | 3/2001 | Deckert et al. |
| 6,213,723 B1 | 4/2001 | Danby et al. |
| 6,213,738 B1 | 4/2001 | Danby et al. |
| 6,231,560 B1 | 5/2001 | Bui et al. |
| 6,269,340 B1 | 7/2001 | Ford et al. |
| D446,854 S | 8/2001 | Cheney, II et al. |
| 6,270,478 B1 | 8/2001 | Mernøe |
| 6,279,248 B1 | 8/2001 | Walters |
| 6,280,416 B1 | 8/2001 | Van Antwerp et al. |
| D447,558 S | 9/2001 | Cartledge et al. |
| 6,297,795 B1 | 10/2001 | Kato et al. |
| 6,299,600 B1 | 10/2001 | Masaoka et al. |
| 6,305,908 B1 | 10/2001 | Hermann et al. |
| D453,830 S | 2/2002 | McDowell et al. |
| 6,347,553 B1 | 2/2002 | Morris et al. |
| 6,348,043 B1 | 2/2002 | Hagen et al. |
| 6,348,952 B1 | 2/2002 | Jeong |
| 6,358,225 B1 | 3/2002 | Butterfield |
| D457,949 S | 5/2002 | Krug et al. |
| 6,398,760 B1 | 6/2002 | Danby |
| 6,413,239 B1 | 7/2002 | Burns et al. |
| 6,423,035 B1 | 7/2002 | Das et al. |
| D461,241 S | 8/2002 | Moberg et al. |
| D461,891 S | 8/2002 | Moberg |
| D462,121 S | 8/2002 | Cartledge et al. |
| 6,458,102 B1 | 10/2002 | Mann et al. |
| 6,471,436 B1 | 10/2002 | Gjata et al. |
| 6,475,180 B2 | 11/2002 | Peterson et al. |
| 6,485,465 B2 | 11/2002 | Moberg et al. |
| 6,489,896 B1 | 12/2002 | Platt et al. |
| 6,500,151 B1 | 12/2002 | Cobb et al. |
| 6,519,569 B1 | 2/2003 | White et al. |
| 6,544,229 B1 | 4/2003 | Danby et al. |
| 6,554,822 B1 | 4/2003 | Holschneider et al. |
| D474,837 S | 5/2003 | Gillespie, Jr. et al. |
| D475,454 S | 6/2003 | Gillespie, Jr. et al. |
| 6,572,604 B1 | 6/2003 | Platt et al. |
| 6,585,675 B1 | 7/2003 | O'Mahony et al. |
| 6,592,551 B1 | 7/2003 | Cobb |
| D479,323 S | 9/2003 | Gillespie, Jr. et al. |
| 6,620,151 B2 | 9/2003 | Blischak et al. |
| 6,648,861 B2 | 11/2003 | Platt et al. |
| 6,652,493 B1 | 11/2003 | Das |
| 6,656,148 B2 | 12/2003 | Das et al. |
| 6,659,980 B2 | 12/2003 | Moberg et al. |
| 6,666,845 B2 | 12/2003 | Hooper et al. |
| 6,692,241 B2 | 2/2004 | Watanabe et al. |
| 6,755,814 B2 | 6/2004 | Wieland et al. |
| 6,776,773 B2 | 8/2004 | Kiyatake et al. |
| 6,800,069 B2 | 10/2004 | Lampropoulos et al. |
| 6,805,687 B2 | 10/2004 | Dextradeur et al. |
| 6,827,702 B2 | 12/2004 | Lebel et al. |
| 6,854,620 B2 | 2/2005 | Ramey |
| 6,945,954 B2 | 9/2005 | Hochman et al. |
| 6,999,854 B2 | 2/2006 | Roth |
| 7,008,403 B1 | 3/2006 | Mallett |
| 7,018,361 B2 | 3/2006 | Gillespie, Jr. et al. |
| 7,022,107 B1 | 4/2006 | Christensen et al. |
| 7,025,226 B2 | 4/2006 | Ramey |
| 7,029,455 B2 | 4/2006 | Flaherty |
| 7,092,796 B2 | 8/2006 | Vanderveen |
| 7,182,750 B2 | 2/2007 | Lampropoulos et al. |
| 7,193,521 B2 | 3/2007 | Moberg et al. |
| 7,232,423 B2 | 6/2007 | Mernøe |
| 7,236,936 B2 | 6/2007 | White et al. |
| 7,255,683 B2 | 8/2007 | Vanderveen et al. |
| 7,306,578 B2 | 12/2007 | Gray et al. |
| 7,322,961 B2 | 1/2008 | Forrest |
| 7,338,464 B2 | 3/2008 | Blischak et al. |
| 7,341,581 B2 | 3/2008 | Mallett |
| 7,347,837 B2 | 3/2008 | Azzolini |
| 7,351,226 B1 | 4/2008 | Herskowitz |
| 7,356,382 B2 | 4/2008 | Vanderveen |
| 7,374,556 B2 | 5/2008 | Mallett |
| D574,016 S | 7/2008 | Yodfat et al. |
| D577,118 S | 9/2008 | Yodfat et al. |
| 7,471,994 B2 | 12/2008 | Ford et al. |
| 7,534,226 B2 | 5/2009 | Mernøe et al. |
| 7,559,926 B1 | 7/2009 | Blischak |
| 7,569,030 B2 | 8/2009 | Lebel et al. |
| 7,601,148 B2 | 10/2009 | Keller |
| 7,608,060 B2 | 10/2009 | Gillespie, Jr. et al. |
| 7,611,498 B2 | 11/2009 | Hasler |
| 7,621,893 B2 | 11/2009 | Moberg et al. |
| 7,632,249 B2 | 12/2009 | Momeni et al. |
| 7,637,892 B2 | 12/2009 | Steinbach et al. |
| 7,647,237 B2 | 1/2010 | Malave et al. |
| D612,484 S | 3/2010 | Yodfat et al. |
| D614,587 S | 4/2010 | Yodfat et al. |
| 7,708,717 B2 | 5/2010 | Estes et al. |
| 7,717,903 B2 | 5/2010 | Estes et al. |
| 7,725,272 B2 | 5/2010 | Ginggen et al. |
| 7,743,975 B2 | 6/2010 | Miller |
| 7,758,552 B2 | 7/2010 | Zoltan et al. |
| 7,766,863 B2 | 8/2010 | Gillespie, Jr. et al. |
| 7,766,873 B2 | 8/2010 | Moberg et al. |
| 7,776,029 B2 | 8/2010 | Whitehurst et al. |
| 7,776,030 B2 | 8/2010 | Estes et al. |
| 7,789,859 B2 | 9/2010 | Estes et al. |
| 7,794,426 B2 | 9/2010 | Briones et al. |
| 7,794,427 B2 | 9/2010 | Estes et al. |
| 7,794,428 B2 | 9/2010 | Estes et al. |
| 7,803,134 B2 | 9/2010 | Sharifi et al. |
| 7,833,196 B2 | 11/2010 | Estes et al. |
| 7,837,651 B2 | 11/2010 | Bishop et al. |
| 7,850,641 B2 | 12/2010 | Lebel et al. |
| 2001/0031944 A1 | 10/2001 | Peterson et al. |
| 2001/0034502 A1 | 10/2001 | Moberg et al. |
| 2002/0004645 A1 | 1/2002 | Carlisle et al. |

(56) References Cited

U.S. PATENT DOCUMENTS

| | | |
|---|---|---|
| 2002/0128606 A1 | 9/2002 | Cowan et al. |
| 2002/0165491 A1 | 11/2002 | Reilly |
| 2003/0009133 A1 | 1/2003 | Ramey |
| 2003/0060754 A1 | 3/2003 | Reilly et al. |
| 2003/0060768 A1 | 3/2003 | Kiyatake et al. |
| 2003/0065287 A1 | 4/2003 | Spohn et al. |
| 2003/0073954 A1 | 4/2003 | Moberg et al. |
| 2003/0078534 A1 | 4/2003 | Hochman et al. |
| 2003/0097092 A1 | 5/2003 | Flaherty |
| 2003/0149402 A1 | 8/2003 | Gerlach et al. |
| 2004/0135078 A1 | 7/2004 | Mandro et al. |
| 2009/0093910 A1 | 4/2009 | Grosz et al. |

FOREIGN PATENT DOCUMENTS

| | | |
|---|---|---|
| EP | 0447985 | 9/1991 |
| EP | 0522527 | 1/1993 |
| EP | 0560270 | 9/1993 |
| EP | 0567944 | 11/1993 |
| EP | 0567945 | 11/1993 |
| EP | 0567946 | 11/1993 |
| EP | 0567962 | 11/1993 |
| EP | 0069350 | 10/2001 |
| GB | 2190145 | 11/1987 |
| GB | 2208897 | 4/1989 |
| GB | 2336510 | 10/1999 |
| WO | WO84/04685 | 12/1984 |
| WO | WO92/03656 | 3/1992 |
| WO | WO93/05829 | 4/1993 |
| WO | WO95/17913 | 7/1995 |
| WO | WO00/42911 | 7/2000 |
| WO | WO00/48112 | 8/2000 |
| WO | WO00/68766 | 11/2000 |

OTHER PUBLICATIONS

International Search Report for International Application No. PCT/US 02/36964 of Applicant Baxter International Inc.

International Search Report for PCT/US2011/042288 dated Nov. 14, 2011.

International Search Report for PCT/US2011/042288 dated Jul. 4, 2012.

First Examination Report for New Zealand Application No. 605828 dated Jul. 30, 2013.

* cited by examiner

TUBE MEASUREMENT TECHNIQUE USING LINEAR ACTUATOR AND PRESSURE SENSOR

BACKGROUND

The field of the present disclosure is infusion pumps and relates generally to systems, apparatuses, and methods for pumping or infusing volumes of medical fluids to a patient, typically via an intravenous route.

Infusion pumps are used to infuse drugs and liquids into patients, typically via intravenous lines. While some infusion pumps pump relatively large volumes, there is an emphasis in the industry for pumps with the capability of precisely delivering small controlled volumes of liquid. Here, the drugs pumped may be very critical to the patient, such as analgesics, anesthetics including opiates, anti-inflammatory agents, insulin, anti-spasmodic drugs, antibiotics, chemotherapy agents, cardiovascular drugs, and the like. Many of these drugs are needed in very low doses on a continuous basis, so that the patient receives a steady, reliable stream over a longer period of time, such as 0.1 ml per hour. Drug pulses may also be used, in which the dosage rate can be measured in terms of nanoliters or microliters per pulse or bolus. In any case, the accuracy of the pump is important to a successful outcome for the patient.

Some infusion pumps have, along the length of tubing, a pumping chamber having an inlet valve and an outlet valve. The infusion fluid is admitted into a length of tubing in the pumping chamber through an opened inlet valve and then isolated by occluding the tube by closing the inlet valve at an inlet of the pump chamber. The outlet valve is then opened and a pumping mechanism compresses the length of tubing in question to pump or expel the fluid from the pumping chamber and towards the patient. Since the inlet is blocked by the closed inlet valve, the liquid can only exit through the outlet of the pumping chamber, through an open outlet valve. The outlet valve is then closed, completing a single pumping cycle or stroke. The inlet valve and pumping mechanism are opened to permit additional fluid to enter the pumping chamber from a fluid source in a next stroke and so on.

The pumping mechanism can comprise a single pumping member that compresses the tube against a stationary block or platen. Alternatively, the pumping mechanism may comprise a plurality of pumping fingers or members that compress the tube in sequence. In this instance, particularly if there are sufficient pumping fingers, such that at least one is compressing the tube at all times, there may be no need for an inlet and/or outlet valve.

The accuracy of the overall infusion is dependent upon the accuracy of each pumping cycle. It is therefore important to know accurately the volume of fluid pumped with each pumping cycle and to know the volume of the entire infusion over time. The volume of each pumping cycle is dependent upon factors such as the tube's internal diameter and the tube's wall thickness. A problem arises due to the variability of internal diameter and wall thickness from tube to tube. This variability is due to, for example, manufacturing processes and tolerances. It would be helpful to provide an infusion pump capable of determining, or measuring the internal diameter and/or wall thickness of the specific IV tube being used for a specific infusion.

SUMMARY

The present disclosure sets forth two primary embodiments for accurately determining the wall thickness of a tubing set loaded into an infusion pump. Knowing the tubing thickness is important to the accurate delivery of a desired volume of a drug to the patient. Based on the tubing wall thickness, the pump can adjust the functionality of the pumping mechanism (speed and stroke length of the pumping mechanism) to ensure and maintain pumped fluid volume accuracy regardless of variances in the tubing thickness or inner diameter. Additionally, the pump can use this information to avoid overly compressing the tube (decreasing tube life due to overstressing) and under compressing the tube (leading to inaccuracies and inefficiencies). The embodiments discussed herein are also financially beneficial because they obtain the wall tubing information without major structural adjustments to the infusion pump.

In one primary embodiment, the tubing thickness is determined by counting encoder pulse counts on a linear actuator as the actuator compresses a tube between two platens of a pump. A motor applies a constant current to the linear actuator until fully compressing the tube. The number of encoder pulses counted until full compression occurs is used to determine the distance traveled by the linear actuator, which is in turn used to determine the thickness of a tube. The constant current applied by the motor is sufficient to compress fully the tube without elastically compressing the tube wall.

In this embodiment, one platen is stationary and one is movable. Moreover, the rate of new encoder pulses decreases and the motor's current increases as the tube approaches full compression, with full compression occurring when no new encoder pulse counts are generated.

Based on the determined tube thickness, a pump controller can adjust at least one parameter of the pump including, for example, pump volume, pump speed, and pump stroke length.

In another primary embodiment, the tubing thickness is determined by measuring the force that the tube exerts on one or more pressure sensors based on zero gas pressure, a known gas pressure, or range of gas pressures, applied to an inside of the tubing. The principle of operation in this embodiment is that for a given pressure, or no pressure, less force will be exerted by a thinner-walled tube on a force or pressure transducer contacting an outside surface of the tube than by a thicker-walled tube.

In this embodiment, a tube is loaded into the pump with the pump pressure sensors contacting the tube's outside wall. The force imparted by the tube outer wall on the pressure sensor can be recorded at 0 psig, before any positive gas pressure is applied to the interior of the tube. This force value is compared with a group of force values, each of which corresponds to a tube of known thickness. Based on this comparison, one can determine the relative thickness of the tube.

Alternatively both ends of the tube can be closed to allow applied gas to build pressure on the inside of the tube. The force imparted by the tube outer wall on the pressure sensor can be recorded on a single, desired positive gas pressure applied to the interior of the tube. This force value is compared with a group of force values, each of which corresponds to a tube of known thickness. Based on this comparison, one can determine the relative thickness of the tube.

In another alternative embodiment, gas pressure can be in the form of a pressure sweep applied to interior of the tube with force values recorded from the pressure sensor at stepwise increments during the pressure sweep. These incremental force values are plotted and compared against a group of predetermined sensor plots to determine the thickness of the tube, with each sensor plot corresponding to a tube of known thickness.

It is accordingly an advantage of the present disclosure to provide a system and method for compensating for tubing manufacturing variations in determining medical fluid volume pumped via a tubing pump.

It is yet another advantage of the present disclosure to provide a method for identifying a tube's thickness with the existing structure of an infusion pump.

It is a further advantage of the present disclosure to provide a method for varying parameters of a pump to increase pump accuracy.

Additional features and advantages are described herein, and will be apparent from the following Detailed Description and the figures.

DETAILED DESCRIPTION

Figure 1:
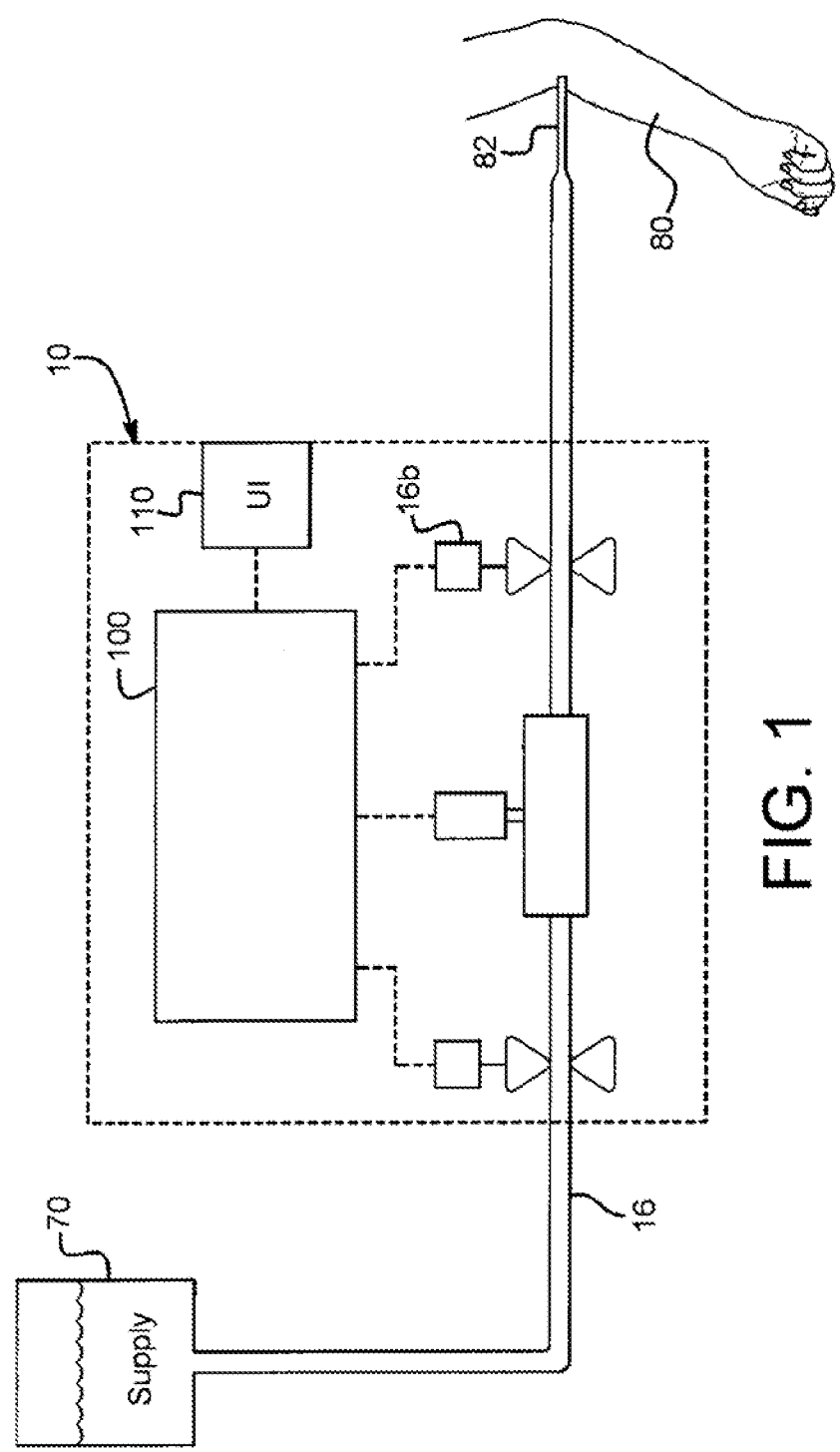
FIG. 1 is a schematic view of a valve and medical flow arrangement for a medical fluid pump and linear actuators and associated valves of the present disclosure.

Referring now to the drawings and in particular to FIG. 1, a schematic illustration of infusion pump 10 is illustrated. Pump 10 pumps a drug or medicament from a supply 70, through a tube 16, to a patient 80, via a patient catheter or cannula 82. Tube 16 as illustrated is loaded into infusion pump 10, so that the pump can pull fluid from supply 70 and move the fluid in a controlled manner through tube 16, via catheter or cannula 82, to patient 80. Infusion pump 10 includes a logic implementer or control unit 100. Control unit 100 includes one or more processors, such as supervisory processor that controls one or more delegate processors, which in turn controls various aspects of infusion pump 10. Control unit 100, for example, can employ a safety or monitoring processor, which ensures that the supervisory processors and delegate control processors are operating properly. The processors operate with one or more memories, which is also part of control unit 100. As shown, control unit 100 operates with or controls a user interface 110. User interface 110 displays information to the patient or operator and allows the patient or operator to enter information from the user interface into control unit 100. To that end, user interface 110 can operate with a touch screen overlay or with one or more electromechanical input devices, such as a membrane switch.

User interface 110 enables the operator to command controller 100 to control infusion pump 10 so as to run: (i) a continuous mode in which pump 10 delivers liquid via tubing 16 to achieve a desired volume at a single flow rate; (ii) an auto-ramp mode in which infusion pump 10 delivers liquid from supply 70 at a rate that gradually increases to a threshold, remains at the threshold rate for a prescribed time, and then gradually decreases; (iii) an intermediate mode in which infusion pump 10 delivers discrete liquid volumes spaced over relatively long periods of time, such as a bolus or volume every three hours; (iv) a custom mode in which infusion pump 10 delivers a unique infusion rate at different time intervals; and (v) a pain-controlled analgesic ("PCA") mode during which patient 80 presses a button causing infusion pump 10 to periodically infuse a bolus of analgesic into the patient.

Figure 2:
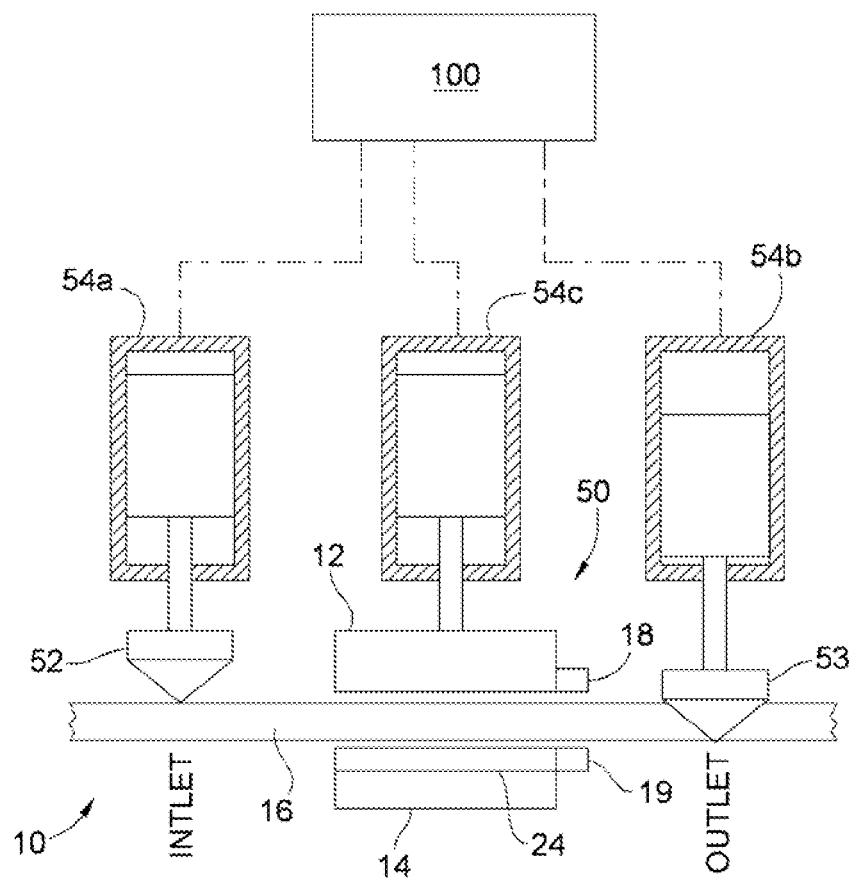
FIG. 2 is an elevation view of a shuttle-type infusion pump having a tubing measurement system and method of the present disclosure.

Referring now to FIG. 2, a pumping portion of the shuttle-type infusion pump 10 of FIG. 1 is illustrated in more detail. Infusion pump 10 includes tube 16, an inlet valve 52, an outlet valve 53, and a shuttle portion 50 having an upper platen 12 and a lower platen 14. Lower platen 14 is parallel to the upper moving platen 12 in the illustrated embodiment. Tube 16 is typically polyvinyl chloride ("PVC"), but may also be made, for example, from polyethylene, polypropylene, another medically acceptable plastic, or a combination of these. Valves 52 and 53 and the shuttle portion 50 are actuated by linear actuators 54a to 54c, respectively. Control unit 100, which again may include multiple processors, such as a supervisory processor, delegate processor, and a safety processor (not shown), controls linear actuators 54a to 54c. That is, the processor, interfacing directly with linear actuators 54a to 54c, may receive commands from a supervisory processor and command actuators 54a to 54c accordingly.

To pump fluid, actuator 54a opens inlet valve 52. Actuator 54b closes outlet valve 53 and actuator 54c retracts movable platen 12, allowing tube 16 to open to receive a liquid medication, e.g., via gravity. This first pump-in position of the infusion pump with opened inlet valve 52 and closed outlet valve 53 is illustrated in FIG. 2. Actuators 54a and 54b then cause the states of valves 52 and 53 to reverse, respectively to a second pump-out position, and actuator 54c pushes platen 12 towards platen 14 to compress tube 16, dispelling the volume of fluid that just filled tubing 16 between platens 12 and 14.

As also illustrated in FIG. 2, a sensor, including a transmitter 18 and a receiver 19 (e.g., radio frequency sensor pair), is imbedded into moving platen 12 and stationary platen 14. The transmitter 18 can be attached to moving platen 12, while the receiver 19 is in turn attached to stationary platen 14. In use, as the shuttle moving platen 12 closes tube 16 to pump the liquid to be infused into the patient, the transmitter 18 and receiver 19 respectively send and receive signals and detect the distance between the transmitter/receiver pair as discussed below. At the same time, a sensor array 24, which is comprised of multiple (e.g., proximity) sensors, can be used to detect the length of the tubing segment in contact with platens 12 and 14. In this manner, sensor pair 18, 19 and sensor array 24 detects and measures the tubing compression distance and contact length, which are sent to control unit 100 to calculate a volume of solution actually pumped. This sensing can be repeated for each pump stroke. Pump controller 100 then integrates the determined volumes to adjust the frequency and/or distance of movement of moving platen 12 to ensure accuracy.

It should be understood that sensor pair 18, 19 and sensor array 24 can have different arrangements and configurations than what is illustrated in FIG. 2. Moreover, sensor pair 18, 19 and sensor array 24 can provide information other than tubing compression distance and contact length as described above. For example, sensor pair 18, 19 can be replaced with a pressure sensor, as will be described below, for measuring a force imparted by tubing 16 onto on platens 12 and 14.

Figures 3A, 3B:
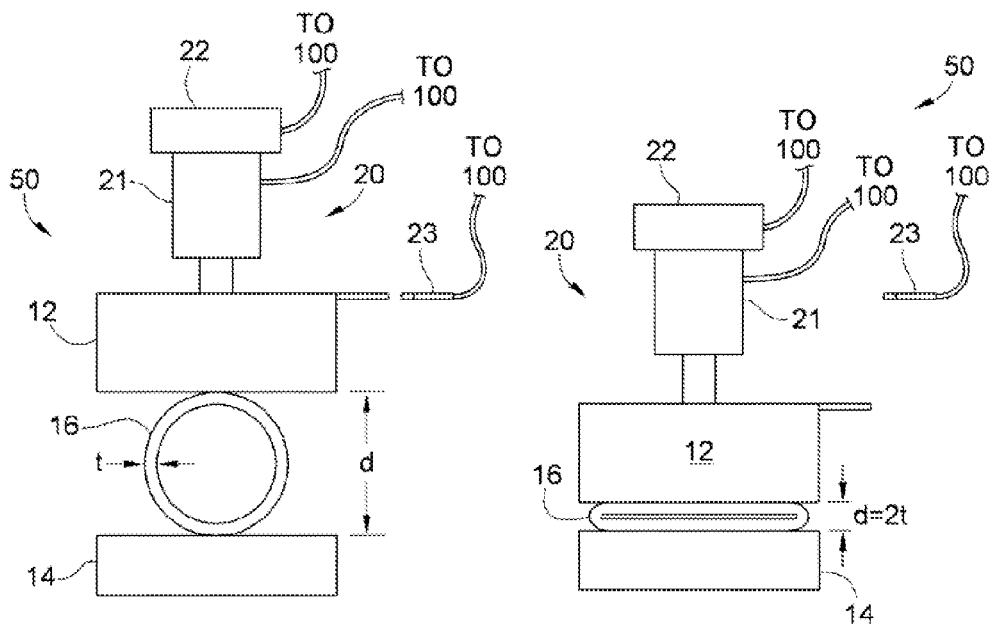
FIGS. 3A and 3B are side views illustrating one tubing measurement system and method embodiment of the present disclosure.

Referring now to FIG. 3A, in one primary embodiment for determining tubing wall thickness, shuttle portion 50 of infusion pump 10 of FIG. 2 is shown from a longitudinal end and includes lower stationary platen 14 and the upper, moving platen 12, which operate to compress and decompress tube 16. Linear actuator 20 in the illustrated embodiment includes an encoder 22 mounted on a motor 21. For example, motor 21 can be a stepper motor or servomotor that is linked to a ball screw or lead screw that transfers rotational motion of the motor to translational motion that carries movable platen 12 towards or away from stationary platen 14. The ball screw has a lead, which is the distance a nut threaded to the lead screw (and attached to platen 12) travels per one revolution of the screw. For example, the lead may be such that one revolution of the shaft of motor 21, and thus the ball screw, results in platen 12 moving 0.1 inch.

The encoder can include a radially spaced apart series of slits that create pulses of light between a light source and a light receiver. If, for example, the encoder includes one hundred slits, the encoder creates one hundred pulses per revolution, that is, turns 1% of a full revolution per pulse. The 0.01 turn per pulse multiplied by 0.1 inches per turn yields 0.001 inches per pulse. Counting pulses (or counts) thus yields a very precise measurement of how far platen 12 has moved towards or away from platen 14.

Motor 21 and encoder 22 are connected to control unit 100, shown in FIGS. 1 and 2, to provide positional information that control unit 100 uses to convert to tube thickness values as discussed below. Control unit 100 controls motor 21 and records data from encoder 22 regarding the angular position of the shaft of motor 21 and converts that rotational position, or change in rotational position, into an accurate calculation of the change in translational position of linear actuator 20 and the distance traveled by platen 12. Beginning from a known position, which can be known from a home position sensor 23, such as a proximity sensor, the travel and position of platen 12 can be determined at any time using the information from the encoder (encoder counts), and tracking and recording distance "d" (see FIG. 3A) over many discrete time segments during the compression or expansion of tube 16.

FIGS. 3A and 3B illustrate one embodiment for determining tube wall thickness. In FIG. 3A, tube 16 is placed between platens 12, 14 of shuttle portion 50 of infusion pump 10, prior to any compression of tube 16. Prior to compression, tube 16 has a wall thickness "t" when placed initially between platens 12, 14, where "d" is the distance between the upper and lower platens 12 and 14.

When the movable platen 12 is closed, tube 16 is compressed. When moveable platen 12 is completely lowered, as shown in FIG. 3B, tube 16 is compressed such that platens 12, 14 are separated by only tube 16 itself, and the distance "d" is twice the thickness "t" of the tubing wall.

As discussed above, once the distance "d" between platens 12, 14 is approximately equal to 2t, or two times the tube thickness, linear actuator 20 can no longer advance platen 12 toward platen 14. As distance "d" approaches a value approximately equal to twice the thickness "t" of the tubing wall, the rate at which encoder 22 generates new encoder pulses will lessen. Control unit 100 will record this lessening rate, thereby providing an indication that tube 16 is nearing full compression. Once linear actuator 20 can move no further, the shaft position of motor 21 also cannot change and the linear actuator stops. At this point, control unit 100 senses a rise in current from motor 21 indicating that tube 16 is compressed fully and encoder 22 stops generating new encoder pulses. The total number of encoder counts recorded from initiation of the linear actuator to the stopping of the linear actuator represents the distance traveled by the linear actuator.

In one embodiment, control unit 100 is configured to provide a constant current to motor 21, such that platen 12 in turn applies a constant force to tubing 16. The level of current is chosen to ensure that tubing 16 in FIG. 3B becomes compressed completely in terms of removing all air or gas between the contacting tubing walls, but such that the thickness of the wall of tubing 16 does not become elastically compressed, yielding a falsely thinner wall thickness.

To identify the thickness of a specific tubing using total encoder counts, the above procedure, illustrated in FIGS. 3A and 3B, is performed for numerous different tubes of known thickness. Based on the encoder count values associated with each tube of known thickness, one can identify the unknown thickness of tube 16 by compressing tube 16, measuring the total encoder counts after linear actuator 20 stops, and comparing that value to the gathered encoder count data for the tubes of known thicknesses.

As shown in Table 1 below, a low thickness tubing ("LL"), a medium thickness tubing ("NOM") and a high thickness tubing ("HH") were selected and tested according to the system and method above to ensure the occurrence and repeatability of the above procedures. Each tube was divided into multiple sections, with each section tested twice using the process described above to gather encoder count data

TABLE 1

|  | Summary | Load | Section 1 | Section 2 | Section 3 | Section 4 | Section 5 | Average |
| --- | --- | --- | --- | --- | --- | --- | --- | --- |
| Tube 1 | HH | 1st | 4108.3 | 4073.1 | 4347.9 | 4054.8 | 3959.9 | 4386.7 |
| Tube 1 | HH | 2nd | 3951.8 | 4142.3 | 3798.6 | 3883.9 | 4048.6 |  |
| Tube 2 | HH | 1st | 4942 | 4979.11 | 4987.667 |  |  |  |
| Tube 2 | HH | 2nd | 4991.333 | 4952.556 | 4965.333 |  |  |  |
| Tube 1 | NOM | 1st | 5114.9 | 5130.9 | 5136.6 | 5132.4 | 5133 | 5128.7 |
| Tube 1 | NOM | 2nd | 5131 | 5100.5 |  | 5139 | 5147.8 |  |
| Tube 2 | NOM | 1st | 5132.11 | 5116.22 | 5141.33 |  |  |  |
| Tube 2 | NOM | 2nd | 5136.556 | 5106 | 5132.889 |  |  |  |
| Tube 1 | LL | 1st | 5151.6 | 5161.8 | 5160.1 | 5158.5 | 5177 | 5168.8 |
| Tube 1 | LL | 2nd | 5116.4 | 5229 | 5054.6 | 5169.3 | 5150.3 |  |
| Tube 2 | LL | 1st | 5141.44 | 5157.667 | 5156 |  |  |  |
| Tube 2 | LL | 2nd | 5242.778 | 5142.778 | 5230 |  |  |  |

Based on the average encoder count information gathered for each tube sample, it is apparent that the greater the encoder count, the less thick the specific tubing tested. Referring to Table 1 above, the average encoder counts for HH, NOM and LL are 4386.7, 5128.7 and 5168.8, respectively. The thicker tube therefore provides a lower encoder count due to a shorter distance "d" traveled by movable platen 12 from a starting position, which corresponds to home position sensor 23, to a final position where tube 16 is fully compressed. Moreover, as stated above, by comparing these average encoder count values to the encoder values of the tubes of known thickness, one can identify the specific thickness of the tubes HH, NOM and LL. Based on the determined thickness of tube 16, control unit 100 can adjust parameters of infusion pump 10 including, for example, pump volume, pump speed and stroke length, which will vary as tube thickness varies.

Figure 4:
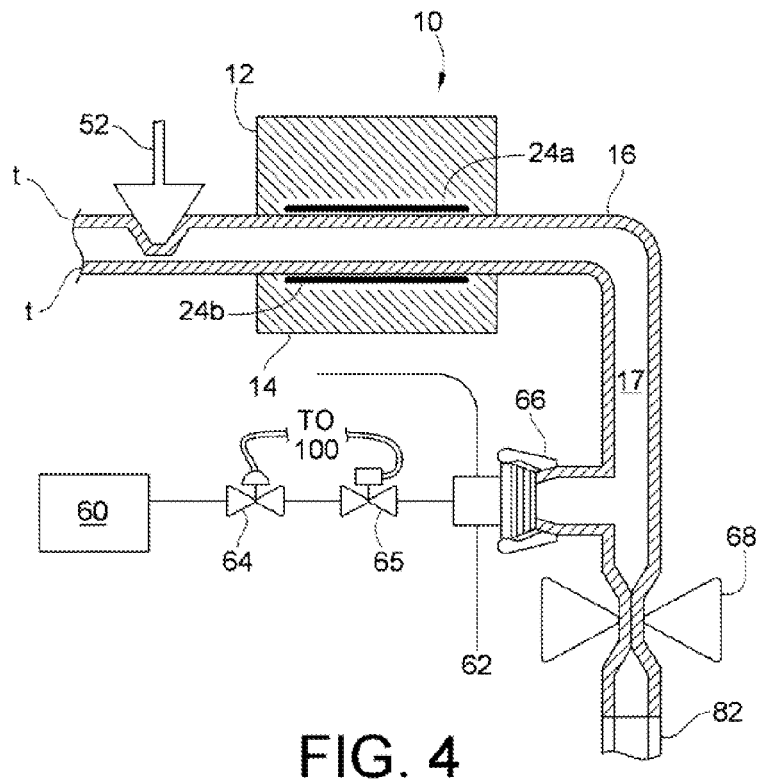
FIG. 4 is a partial cross-sectional view illustrating another tubing measurement system and method embodiment of the present disclosure.

FIG. 4 illustrates another primary embodiment for determining tube thickness. Here, tubing 16 is loaded between platens 12 and 14, and the resulting force applied by the outside of tubing 16 to platens 12 and 14 is measured. Alternatively, the inside of tubing 16 is pressurized with a gas, and the resulting force applied by the outside of tubing 16 to platens 12 and 14 is measured. In either case, the thicker the tubing, the more force that is transferred. In FIG. 4, tube 16 is placed again between platens 12, 14 of the infusion pump. Platen 12 does not need to be moved in this embodiment. Each platen 12 and 14 includes a force or pressure sensor 24a, 24b on its respective face that contacts tube 16. One suitable pressure sensor is provided by Honeywell, Model No. FSL05N2C. It should be understood that pressure sensors 24a, 24b can be located alternatively on a single platen 12 or 14 rather than split onto both platens 12 and 14 as is illustrated.

FIG. 4 also illustrates a pressurized gas source 60 connected fluidly to a port 62, wherein flow from a gas source 60 to nozzle 62 is controlled via a gas flow controller 64. The gas may be, for example, compressed nitrogen, air or other compressed gas supply provided at a hospital. Gas controller 64, for example, may be an electronically controlled pressure regulator that is opened and closed as needed by pump control unit 100. Gas flow controller 64 creates a desired downstream pressure inside tubing 16. An electrically or manually controlled shut-off valve 65 may be provided alternatively or additionally. Although not shown, one or more pressure gauges for reading pressure in the gas line may be provided.

In one alternative embodiment, gas source 60 is a cylinder of compressed gas, which is connected to infusion pump 10. In a further embodiment, gas source 60 is instead an air pump within pump 10 that control unit 100 powers when called upon to pressurize tube 16. In any case, pump 10 houses gas regulator 64 and valve 65, which selectively allow pressurized gas to flow through port 62 into tube 16.

In operation, the nurse or practitioner loads a tube 16 between platens 12 and 14 of a pump 10. At this point, a 0 psig internal pressure exists on the inside of tube 16. However, tube 16 still imparts a force that is recorded by sensors 24a and 24b. The force value represents the amount of force tube 16 imparts on the walls of platens 12 and 14, which control unit 100 can use to compute a tube thickness as will be discussed below with reference to FIG. 5.

Alternatively, the nurse or practitioner can connect a cap 66 of tube 16 to port 62 of gas source 60 to establish gas communication. Inlet end of tube 16 is clamped via pinch valve 52, while catheter 82 end of tube 16 is clamped via manual clamp 68 to create a sealed tubing volume. Gas source 60 then injects air through port 62 into an interior 17 of tube 16, which can be in the form of a single pressure or a pressure sweep.

In the case of a single pressure, control unit 100 controls regulator 64 and valve 65 to inject gas into interior 17 of tube 16 at, for example, a single pressure. Sensors 24a and 24b then record a force value representing the amount of force that tube 16 imparts on the walls of platens 12, 14. Control unit 100 uses the force value to compute a tube thickness as will be discussed below with reference to FIG. 5.

In the case of a pressure sweep, control unit 100 controls regulator 64 and valve 65 to inject gas into interior 17 of tube 16 at step-wise rising pressures from a minimum value to a maximum value. At the specific pressure increments during this pressure sweep, sensors 24a and 24b record a force value representing the amount of force that tube 16 imparts on the walls of platens 12, 14. Upon completing the pressure sweep, control unit 100 uses the force values to compute a tube thickness as will be discussed below with reference to FIG. 5.

Figure 5:
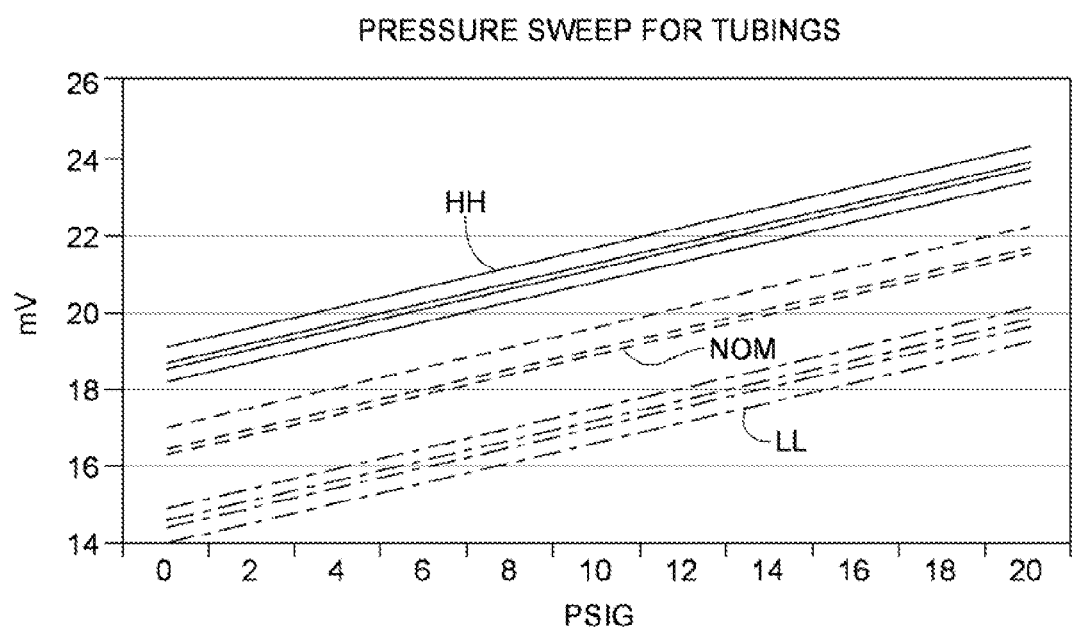
FIG. 5 is a graph illustrating force values taken from a force sensor for different tubings across a pressure sweep recorded to identify specific wall thicknesses based on the tubing measurement system and method embodiment of FIG. 4.

FIG. 5 illustrates pressure sweeps taken for various tubings, particularly a low thickness tubing ("LL"), a normal thickness tubing ("NOM") and a high thickness tubing ("HH"). Multiple samples of each size tube were inserted between platens 12 and 14 of infusion pump 10, with each tube having one end clamped and the interior of the tube injected with a gas through the open end of the tube. The gas was injected at controlled levels up to 20 psig, with force values recorded at every 1-psig increment starting at 0 psig before any gas injection. These values were plotted on the line chart of FIG. 5. Pressure sweeps can have higher maximum values of 25 psig or even higher as necessary. The defined pressure increments for recording force values can also vary as necessary to gather enough data to plot against the associated force values.

As is apparent from FIG. 5, very little variability exists between the different sample tubes having the same thickness. However, a clear offset is observed between tubing thicknesses, with HH tubes returning significantly greater force values than LL tubes or even NOM tubes. Based on this chart, one could identify a high thickness tube versus a normal thickness tube versus a low thickness tube. Further, as discussed above, by comparing a single plotted force value against plotted force values of tubes of known thickness, pump 10 can automatically identify the specific type of thickness tube HH, NOM and LL that has been inserted into pump 10.

To identify tube thickness without gas injection, FIG. 5 illustrates that, at 0 psig, LL tube has a force range from approximately 14 to 15 mV, NOM tube has a force range from approximately 16 to 17 mV, and an HH tube has a force range from approximately 18 to 19 mV. Therefore, even at 0 psig, different tube thicknesses impart different forces such that one can distinguish between the tubes and, as a result, determine tube thickness.

When determining tube thickness using a single gas pressure, gas flow controller 64 would not have to be an electrically variable type and could instead be set, e.g., manually, to yield a set test pressure. For example, FIG. 5 shows that, at 15 psig, an LL tube has a force range from approximately 18 to 19 mV, NOM tube has an initial force range of 20 to 21 mV and HH has an initial force range between 22 to 23 mV. Given the known ranges illustrated in FIG. 5, if a tube of unknown thickness type is inserted between platens 12 and 14, pump 10 can determine the thickness type of the tube if the force value of tube 16 is within the ranges described above at the single, desired positive pressure of 15 psig.

When determining tube thickness using a sweep of pressures, the corresponding force values can be plotted to form a resulting line of points, which pump 10 can compare to predetermined lines of points such as, for example, the lines for LL, NOM and HH tubes of known thickness. Pump 10 can determine the thickness type of the tube if the force values, from the pressure sweep of tube 16, are within any of the plotted pressure sweeps illustrated in FIG. 5.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A method of measuring tube wall thickness, the method comprising:
   loading a tube between a stationary member and a movable member;
   compressing the tube between the stationary member and the movable member;
   receiving a signal indicative of an amount of compression of the tube while compressing the tube; determining from the signal that the tube is fully compressed and stopping the compressing of the tube once the tube is fully compressed; and
   determining a thickness of the tube wall based on the signal received indicating full compression.

2. The method of claim 1, wherein the stationary member and the movable member are part of an infusion pump.

3. The method of claim 1, wherein receiving the signal includes counting encoder pulses.

4. The method of claim 3, wherein determining that the tube is fully compressed includes determining that no new encoder pulses are being generated.

5. The method of claim 3, wherein determining that the tube is fully compressed includes determining a rate at which new encoder pulses have lessened.

6. The method of claim 1, wherein compressing the tube includes providing a constant current to a motor sufficient to allow the tube to be fully compressed without elastically compressing the tube.

7. The method of claim 1, wherein receiving the signal includes receiving a current draw signal and determining that the tubing is fully compressed includes sensing a current rise.

8. The method of claim 1, further comprising setting at least one infusion pump parameter based upon the determined tube thickness.

9. A method of measuring tube wall thickness, the method comprising: providing a fixture having a loading portion and a pressure sensor, the pressure sensor located on a wall of the loading portion; loading a tube into the loading portion such that the tube imparts a force on the pressure sensor that contacts an outside wall of the tube; recording the force imparted on the pressure sensor by the outside wall of the tube; and determining the thickness of the tube wall based on the force imparted by the tube on the pressure sensor.

10. The method of claim 9, wherein the step of determining the thickness of the tube includes comparing the force imparted by the tube with a plurality of force values, each force value corresponding to a specific tube having a predetermined thickness.

11. The method of claim 9, wherein the thickness of the tube is determined as a relative thickness selected from the group consisting of low tube thickness, moderate tube thickness and high tube thickness.

12. The method of claim 9, wherein the fixture is an infusion pump.

13. The method of claim 9, further comprising applying a positive pressure to the interior of the tube.

14. A method of measuring tube wall thickness, the method comprising: providing a fixture having a loading portion and a sensor, the sensor located on a wall of the loading portion; loading a tube into the loading portion, wherein the sensor contacts an outside wall of the tube; applying a pressure sweep to the interior of the tube,
   wherein the pressure sweep starts at a minimum value and ends at a maximum value;
   recording a plurality of output values from the sensor, each output value recorded at step-wise increments during the pressure sweep; and determining the thickness of the tube wall based on the output values recorded during the pressure sweep.

15. The method of claim 14, the method further comprising closing both ends of the tube before applying the pressure sweep to the tube.

16. The method of claim 14, wherein the minimum value is zero psig.

17. The method of claim 14, wherein the maximum value is 25 psig.

18. The method of claim 14, wherein the step-wise increments are at every one psig during the pressure sweep.

19. The method of claim 14, wherein the fixture is an infusion pump.

20. The method of claim 14, wherein the step of determining the thickness of the tube comprises:
   plotting the plurality of output values along the pressure sweep to produce a sensor plot for the tube; and
   comparing the sensor plot with a plurality of predetermined sensor plots, each predetermined sensor plot corresponding to a specific tube having a predetermined thickness.

21. A method of measuring tube wall thickness, the method comprising:
   loading a tube between a stationary member and a movable member; compressing the tube between the stationary member and the movable member; receiving a signal indicative of an amount of compression of the tube while compressing the tube;
   determining from the signal that the tube is fully compressed and stopping the compressing of the tube once the tube is fully compressed; and determining a thickness of the tube wall based on the signal received indicating full compression, wherein receiving the signal includes receiving a current draw signal and determining that the tubing is fully compressed includes sensing a current rise.

* * * * *